United States Patent [19]
Faupel et al.

[11] Patent Number: 5,560,357
[45] Date of Patent: *Oct. 1, 1996

[54] D.C. EPIDERMAL BIOPOTENTIAL SENSING ELECTRODE ASSEMBLY AND APPARATUS FOR USE THEREWITH

[75] Inventors: Mark L. Faupel, Conyers, Ga.; Steven Hahn, deceased, late of East Hampton, N.Y., by Natalie A. Hahn, executrix

[73] Assignee: Biofield Corp., Roswell, Ga.

[ * ] Notice: The term of this patent shall not extend beyond the expiration date of Pat. No. 5,415,164.

[21] Appl. No.: 379,994

[22] Filed: Jan. 27, 1995

Related U.S. Application Data

[60] Division of Ser. No. 27,539, Mar. 8, 1993, Pat. No. 5,415,164, which is a continuation-in-part of Ser. No. 787,641, Nov. 4, 1991, Pat. No. 5,217,014.

[51] Int. Cl.$^6$ ........................................ A61B 5/00
[52] U.S. Cl. .......................................... 128/635; 607/901
[58] Field of Search .................... 128/635, 639, 128/640, 642, 641, 657, 734; 604/20; 607/901

[56] References Cited

U.S. PATENT DOCUMENTS

| | | | |
|---|---|---|---|
| 3,580,239 | 5/1971 | Watanabe et al. | 128/639 |
| 4,034,854 | 7/1977 | Bevilacqua . | |
| 4,037,267 | 7/1977 | Kisor . | |
| 4,082,086 | 4/1978 | Page et al. | 128/640 |
| 4,220,159 | 9/1980 | Francis et al. | 128/639 |
| 4,328,809 | 5/1982 | Hirschowitz et al. . | |
| 4,365,634 | 12/1982 | Bare et al. . | |
| 4,407,300 | 10/1983 | Davis | 128/734 |
| 4,816,130 | 3/1989 | Karakelle et al. | 128/635 |
| 4,834,103 | 5/1989 | Heath | 128/641 |
| 4,836,907 | 6/1989 | Pedersen | 128/635 |
| 4,932,410 | 6/1990 | Lacourciere et al. | 128/635 |
| 4,953,552 | 9/1990 | De Marzo | 128/635 |
| 4,975,175 | 12/1990 | Karube et al. | 128/635 |
| 4,995,391 | 2/1991 | Jensen et al. | 128/635 |
| 5,035,791 | 7/1991 | Battilotti et al. . | |
| 5,042,498 | 8/1991 | Dukes | 128/641 |
| 5,099,844 | 3/1992 | Faupel | 128/653.1 |
| 5,257,631 | 11/1993 | Wilk | 128/639 |
| 5,415,164 | 5/1995 | Faupel | 128/630 |

Primary Examiner—William E. Kamm
Attorney, Agent, or Firm—Sixbey, Friedman, Leedom & Ferguson

[57] ABSTRACT

The apparatus and method for screening and diagnosing trauma or disease in body tissues involves the use of DC biopotential sensing electrodes having DC offset potentials within an acceptable range and electrical characteristics which enhance the accuracy of the biopotential measurement. The apparatus checks the electrodes connected thereto prior to a measurement cycle and will not initiate the measurement cycle if improper electrodes are present. The electrodes may be formed to selectively pass only certain ions thereby enhancing the sensitivity of the electrodes.

6 Claims, 5 Drawing Sheets

D.C. EPIDERMAL BIOPOTENTIAL SENSING ELECTRODE ASSEMBLY AND APPARATUS FOR USE THEREWITH

This application is a division of U.S. Ser. No. 08/027,539 filed Mar. 8, 1993, now U.S. Pat. No. 5,415,164 which is a continuation-in-part of U.S. patent application Ser. No. 07/787,641 filed Nov. 4, 1991 now U.S. Pat. No. 5,217,014.

TECHNICAL FIELD

The present invention relates generally to an apparatus and method for the screening and/or diagnosing of a traumatic condition in the body tissues of a living organism by detecting the potential of an electromagnetic field present between a reference point and one or more test points on the living organism to measure the gradient of electrical or magnetic activity which occurs as a function of underlying biological activity, and more particularly to an apparatus which operates only when potential detecting electrodes suitable for accurately detecting the electric field present on the tissue or skin of a living organism are connected to the measuring unit for the apparatus.

BACKGROUND ART

In recent years the theory that measurement of the potential level of the electromagnetic field of a living organism can be used as an accurate diagnostic tool is gaining greater acceptance. Many methods and devices for diagnosing diseases have been developed in an attempt to implement this theory. For example, U.S. Pat. No. 4,328,809 to B. H. Hirschowitz et al. deals with a device and method for detecting the potential level of the electromagnetic field present between a reference point and a test point of a living organism. Here, a reference electrode provides a first signal indicative of the potential level of the electromagnetic field at the reference point, while a test electrode provides a second signal indicative of the potential level of the electromagnetic field at the test point. These signals are provided to an analog-to-digital converter which generates a digital signal as a function of the potential difference between the two, and a processor provides an output signal indicative of a parameter or parameters of the living organism as a function of this digital signal.

Similar biopotential measuring devices are shown by U.S. Pat. Nos. 4,407,300 to Davis, and 4,557,271 and 4,557,273 to Stoller et al. Davis, in particular, discloses the diagnosis of cancer by measuring the electromotive forces generated between two electrodes applied to a subject.

Unfortunately, previous methods for employing biopotentials measured at the surface of a living organism as a diagnostic tool, while basically valid, are predicated upon an overly simplistic hypothesis which does not provide an effective diagnosis for many disease states as well as other trauma causing conditions. Prior methods and the devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated on or near the disease site to provide a measurement of the polarity of the signal received from the site relative to that from the reference site. When multiple measuring electrodes have been used, their outputs have merely been summed and averaged to obtain one average signal from which a polarity determination is made. This approach is subject to major deficiencies which lead to diagnostic inaccuracy.

First, the polarity of diseased tissue underlying a recording electrode has been found to change over time. This fact results in a potential change which confounds reliable diagnosis when only one recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

As disease states such as cancer progress, they produce local effects which include changes in vascularization, water content, and cell division rate. These effects alter ionic concentrations which can be measured at the skin surface. Other local effects, such as distortions in biologically closed electrical circuits, may also occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). Once this fact is recognized, it follows that important electrical indications of disease are going to be seen in the relative voltages recorded from a number of sites at and near a diseased area, and not, as previously assumed, on the direction (positive vs. negative) of polarity. Methods and devices for effectively performing such disease diagnosis and screening have been developed as illustrated by U.S. Pat. Nos. 4,955,383 and 5,099,844 to M. L. Faupel.

For all biopotential measurements where DC electrical signals are recorded using tissue contacting electrodes, regardless of the measuring instrumentation and method employed, the accuracy of the resulting measurement is extremely dependent upon the electrodes used and the presence or absence of DC offset potentials in these electrodes. Small DC offset potentials can be tolerated in electrodes used to sense AC potentials, such as those employed for electrocardiograms, but where the biopotentials sensed are small DC potentials, DC offset potentials in the electrodes of only a few millivolts can significantly affect the accuracy of any measurement taken with the electrodes.

Many electrodes are packaged in a pre-gelled state wherein an electrolytic paste or gel is packaged as part of the electrode. The gel may be located in a central gel reservoir consisting of a molded cup, or it may be contained in a dye-cut hole in a foam which encapsulates a gel saturated open cell compressible foam column, such as U.S. Pat. No. 3,868,946. In most instances, the pre-gelled electrodes are sold ready for use with an electrically conductive material such as metal or a metal chloride in contact with the electrolyte gel.

A pre-gelled electrode is a battery by itself, but the battery effect cannot be measured unless two such electrodes are placed face to face with the gels for each electrode in contact relationship. In the use of such electrodes, a complex battery is formed consisting of many interactive components including the electrode material (frequently silver/silver chloride), the electrode gel, internal body chemistry and external skin conditions, skin preparation, temperature, air condition and chemistry, etc. Obviously, some of these factors are not subject to control, but in order to get the best data possible, especially in instances where DC biopotentials are of interest, artifacts, such as DC offsets, should be reduced to the lowest level. Clearly, pre-gelled electrodes can possibly present such undesired DC voltage artifacts which should be limited to the lowest voltage possible; ideally zero volts. Most pre-gelled electrodes when introduced in the battery system outlined above contribute some unwanted DC voltage (polarization effect) to biopotential measurement. This is particularly true when two or more pre-gelled electrodes are packaged in face to face contact with the electrolyte gel of opposed electrodes in contact as illustrated by U.S. Pat. No. 4,034,854, to A. J. Bevilasqua, for now a true battery, is formed and polarization will occur. It is important to lower the possibility of such DC artifacts occurring in a degree sufficient to have a substantial adverse effect on DC biopotential measurements, and U.S. Pat. No. 5,217,014 entitled Depolarized Pre-Gelled Electrodes discloses methods and various devices for effectively accomplishing this purpose.

Even when the most accurate and advanced instrumentation for measuring and diagnosing or screening for a disease or tissue injury condition is used, inaccurate readings can result if the electrodes connected to the measuring instrument cannot provide a signal which accurately represents a sensed DC biopotential. Since the electrodes used are replaceable electrodes, it is important that before initiating each DC biopotential measurement operation, it is positively determined that proper electrodes with an acceptable DC voltage artifact are connected to the measuring instrument.

DISCLOSURE OF THE INVENTION

It a primary object of the present invention to provide a novel and improved apparatus and method for taking biopotential measurements and analyzing such measurements to provide disease diagnosis and screening or an indication of traumatic tissue insult. In a start up period prior to the initiation of a measurement operation, the measuring electrodes are checked to ascertain whether or not the electrodes used and/or the electrical condition of such electrodes will permit an accurate measurement to be taken.

Another object of the present invention is to provide a novel and improved apparatus for providing an analysis for cancer or other traumatic insult diagnosis or screening. Relative DC biopotentials are recorded from a number of sites at and near a potentially diseased or traumatized area using an electrode array. An analysis is then used to determine the relationships between the recorded information taken from such sites, and subsets of these relationships may be used to provide a diagnosis of either the presence or absence of a serious condition. Before a biopotential measurement can be initiated, the apparatus checks the electrode array connected thereto to ascertain whether or not the electrodes used and/or the electrical condition of such electrodes will permit an accurate measurement to be taken. If improper electrodes or an improper electrode condition is sensed, no biopotential measurement operation is initiated.

A further object of the present invention is to provide a novel and improved electrode unit for use with an apparatus for taking biopotential measurements which includes at least one unique identifier operative when the electrode unit is connected to the apparatus to identify the electrode unit in response to interrogation by the apparatus.

A still further object of the present invention is to provide a novel and improved method and apparatus operative to screen for, or detect cancer or other tissue insult conditions by sensing DC biopotentials. In a start up period prior to the initiation of a measurement operation the measuring electrodes are checked to ascertain whether or not the electrodes used and/or the condition of such electrodes will permit an accurate measurement to be taken. Then sampling measurements are taken over a monitoring period to determine whether or not all of such measurements fall within a predetermined tolerance of an average reading.

BEST MODE FOR CARRYING OUT THE INVENTION

Figure 1:
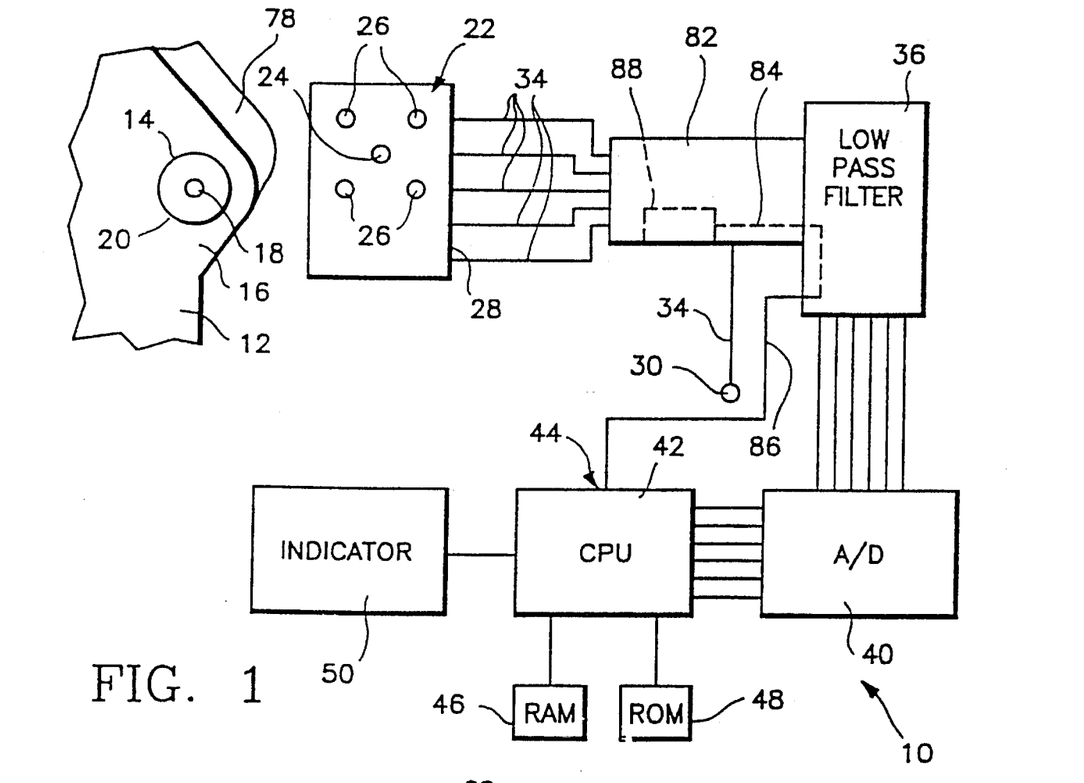
FIG. 1 is a block diagram of the Apparatus For Screening And Diagnosing Trauma Or Disease In Body Tissues of the present invention.

FIG. 1 discloses a basic block diagram of the apparatus of the present invention indicated generally at 10 for performing an analysis for disease or trauma in tissue screening or diagnosis. For purposes of illustration, the apparatus 10 will be described in connection with methods involving the screening for, or diagnosing of breast cancer. However, it should be recognized that the method and apparatus of the present invention can be similarly employed for screening or diagnosis at other disease or trauma sites involving other portions or organs of a living human or animal.

In FIG. 1, a human subject 12 may have a cancerous lesion 14 on one breast 16. This cancerous lesion has a core 18 and an outer zone 20 surrounding the core where various differing local effects, such as changes in vascularization, water content and cell division rate occur. Assuming first, for purposes of discussion, that the location of the lesion 14 is now known, and the device 10 is to be used to screen the breast 16 to determine whether or not a disease condition exists, skin surface potentials will be measured in an area of the breast, including the zone 20 using an electrode array 22. In FIG. 1, the electrode array includes a central electrode 24 surrounded by four peripheral electrodes 26, all of which are epidermal electrodes. However, this invention contemplates the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. For breast cancer screening (where patients are asymptomatic), the array should give maximum coverage of the entire breast surface. The aim in both of these cases is to measure the gradient of electrical activity which occurs as a function of the underlying biological activity of the organ system. The number of electrodes used in the measurement will also be a function of specific application, and breast cancer screening may require the use of as few as twelve or as many as forty or more electrodes for each breast, while in screening for prostate cancer, as few as two measurement electrodes might be used.

The core electrode 24 and the peripheral electrodes 26 are mounted upon a flexible backing sheet 28 which permits the electrodes to be positioned against the curved surface of the breast 16 while still maintaining the position of the electrodes in predetermined pattern. However, other electrode arrays may be employed wherein each individual electrode can be individually positioned, and the relative position between electrodes can be altered. The electrode array 22 is used in conjunction with one or more reference epidermal electrode 30, and all of these electrodes may be of a type used for detecting the potential level of the electromagnetic field present in a living organism. Ideally, the electrodes 24, 26 and 30 should be of a type which do not cause a substantial battery effect between the organism under test and the electrode. Electrodes or electrode arrays suitable for use as the electrodes 24, 26 and 30 are illustrated in FIGS. 2, 8, 9, 10 and 11.

The device 10 is shown as a multi-channel device having electrode leads 34 extending separately from the central electrode 24, the peripheral electrodes 26, and the reference electrode 30 to a low pass filter 36. This filter operates to remove undesirable high frequency AC components which appear on the slowly varying DC voltage signal outputs provided by each or the electrodes as a result of the electromagnetic field measurement. The low pass filter 36 may constitute one or more multiple input low pass filters of known type which separately filter the signals on each of the input leads 34 and then pass each of these filtered signals in a separate channel to a multiple input analog-to-digital converter 40. Obviously, the low pass filter 36 could constitute an individual low pass filter for each of the specific channels represented by the leads 34 which would provide a filtering action for only that channel, and then each filtered output signal would be connected to the input of the analog-to-digital converter 40. Alternatively, as is known, the electrodes may be connected to a single channel filter and a single input analog-to-digital converter and the electrodes would be multiplexer to provide sequential outputs over the single channel to the filter.

Regardless of whether single or multiple channels are used, the analog-to-digital converter 40 converts each analog signal received thereby to a digital signal which is provided to the input of a central processing unit 42. Of course, for some applications, the central processing unit may respond directly to analog input signals or to digital or other coded signals produced directly by the electrode array 22, and in such cases, the analog to digital converter 40 and possibly even the filter 36 would be eliminated and the output from the electrode array would input directly to the CPU. The central processing unit is a component of a central control unit indicated generally at 44 which includes RAM and ROM memories 46 and 48. Digital input data from the analog-to-digital converter 40 is stored in memory and is processed by the CPU 42 in accordance with a stored program to perform the diagnostic and scanning methods of the present invention. The information derived by the CPU as a result of this processing is then fed to a suitable indicator device 50 which may constitute a printer, a CRT display device, or a combination of such conventional indicators.

The electrode array 22 and electrode 30 are critical components in the combination which forms the apparatus 10 and consequently will be considered in detail. The reference electrode 30 and the one or more measuring electrodes 24 and 26 must be substantially devoid of even very minute DC offset potentials when they are applied to a living organism for measurement purposes since a small DC biopotential measurement is to be taken by these electrodes. To measure the DC offset potential which may be present in such electrodes, an electrode pair must be placed in face to face relationship with the gel for one electrode in contact with the gel for the second electrode. With the electrodes so oriented, an offset potential measurement can be taken across the output terminals of the electrodes constituting the electrode pair, and the measured offset potential must be 1.0 millivolt or less if the electrodes are to be used to obtain an accurate DC biopotential measurement.

Figure 2:
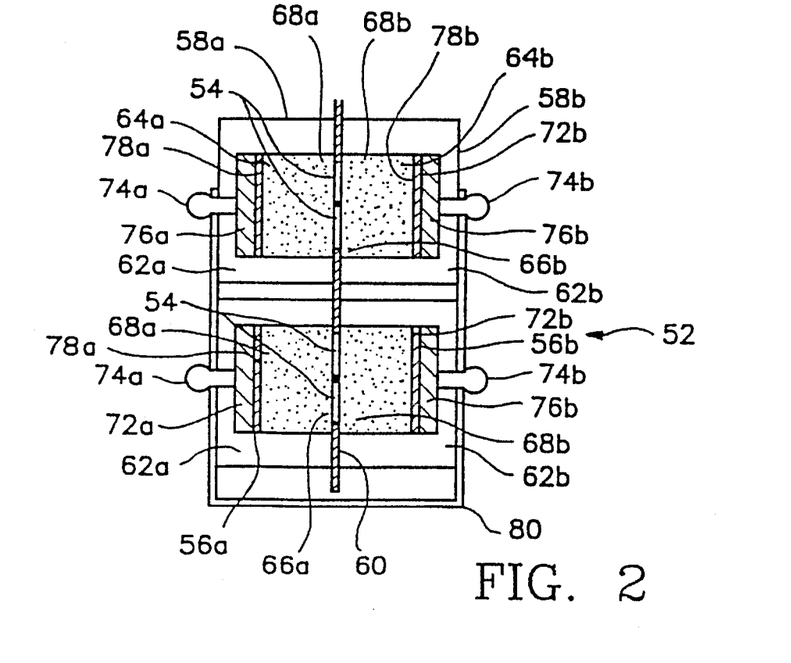
FIG. 2 is a cross sectional view of a depolarized pre-gelled electrode array for use with the present invention.

FIG. 2 illustrates a very desirable structure for shorting the pre-gelled electrodes used in an electrode array during storage and shipment and prior to use to depolarize the electrodes in the array and reduce or eliminate offset potentials in the electrodes. Electrodes short circuited in this manner prior to use can be effectively used in the electrode array 22 to provide accurate biopotential measurements. An array 52 of four electrodes is illustrated for purposes of description in FIG. 2, but obviously any number of electrodes can be connected together and depolarized in like manner. The electrode array includes electrode pairs including pre-gelled electrodes 56a and 56b and pre-gelled electrodes 58a and 58b mounted face to face and held together by a nonconductive carrier 60 of Mylar or similar material. The Mylar carrier 60 extends between the electrodes of each electrode pair and permits subsequent separation of the electrodes. Holes 54 formed in the Mylar permit full contact between the electrolyte gel in the electrodes 56a and 58a and the gel in the opposing electrodes 56b and 58b. The components of each electrode are identified and will be given the same reference numbers differentiated by the letters "a" and "b".

Each electrode includes a support member 62 which forms an insulating cup 64 open at one end 66 and which receives electrolyte gel 68 which is preferably a wet electrolyte gel. The carrier 60 extends across the open ends of the support members for each electrode and is provided with the openings 54 which permit the gel 68 in each electrode to make electrical contact with the gel in the opposing electrode. These openings should be as large as possible to permit full contact between the electrolyte gels 68a and 68b while still facilitating the subsequent separation of the electrodes 56a, 58a, 56b and 58b.

In contact with the electrode gel in each insulating cup is an electrode element 72 having a projecting snap button cable connector or terminal 74 for connection to an external cable. Each electrode element 72 may include a silver layer 76 and a silver chloride layer 78 or other conventional electrode element forming materials. The diameter of the electrode element 72 used for the array 22 is preferably about 0.417 inches and the electrodes 24 and 26 are preferably spaced apart about 1.25 inches center to center.

Therefore the spacing ratio to electrode element diameter is substantially 3 to 1.

The array 52, due to its configuration, constitutes a true battery and this battery is electrically short circuited during shipment and storage by a conductive wire or strip 80 electrically connected between the terminals 74a & b of all electrodes. This conductive wire or strip shorts the potential battery and brings the electrode elements to a stable, near zero volt DC level. Prior to use, the conductive wire or strip 80 is removed and the electrode array now at near a zero DC level, may be separated from the carrier 60 and immediately placed on a patient for bioelectric measurement purposes. After the wire or strip is removed, the electrodes should be promptly used, for if they are left unshorted they may once again develop unwanted DC offset potentials.

It is important that no biopotential measurements be taken using the device 10 if a depolarized electrode array is not connected to provide the electrode array 22 and the reference electrode 30. One structure for accomplishing this incorporates the leads 34 into a cable 82 which is used to removably connect the electrode array 22 and the reference electrode 30 to the low pass filter 36. This cable can be a multichannel cable or a single channel cable, depending upon whether or not electrode multiplexing is employed. A conventional connector, not shown, is provided to connect one end of the cable to the low pass filter 36, or with a single channel filter, the connector is plugged to a sequencing switch. Each cable lead 34 is connected to the terminal 74 for one of the electrodes in the depolarized electrode array 52. This is done when the electrode array 52 is formed, and the shorting strip 80 is designed so that it may be removed without disturbing the connected leads 34.

When the cable 82 is connected to the low pass filter 36, a separate connection is made between a conductor 84 within the cable and a conductor 86 leading directly to the CPU 42. The conductor 84 leads to an address identification chip 88 of known type which responds to an address interrogation signal provided over the conductor 84 to the address chip. The proper address interrogation signal is stored in the memory for the central control unit 44 and is sent over the conductor 86 by the CPU 42 when the apparatus 10 is initially activated. If this interrogation signal corresponds to a signal to which the address chip 88 responds, then a response from the address chip is passed by the conductors 84 and 86 back to the CPU 42 and the CPU continues with a measurement operation in response to a control program stored in the memory for the central control unit. Alternatively, if the wrong address chip, no address chip or no electrode array connection is present, no response is received from the address interrogation signal and the CPU 42 does not proceed with the stored control program.

In addition to the address chip 88, the central control unit 44 can be made responsive to other parameters in the electrode array 22 during an initialization period to assure that an acceptable electrode array is in place before a measurement program is begun. As has been previously indicated, the presence of an offset potential in the electrode array is detrimental to the accuracy of DC biopotential measurements, and the magnitude of this offset potential can be measured during the initialization period of the apparatus 10. To accomplish this, the cable 82 is connected to the filter 36 or to a sequencer switch with the shorting strip 80 preferably still in place on the electrode array 52. Now, any offset potential present in any pair of electrodes in the electrode array can be measured by the control unit 44 in the same manner that a biopotential from the electrode array will be sensed after the initialization period is terminated. If the measured offset potential is less than a predetermined level, then the CPU may continue with a measurement operation in response to the stored control program once the shorting strip 80 is removed from the electrode array and the array is secured to a test area or a subject. However, if the offset potential exceeds the predetermined level, the measurement operation is not initiated by the CPU.

The electrodes which are used as the electrodes 24, 26 and 30 should be manufactured to specific electrical tolerances if they are to be effectively used to provide accurate DC biopotential measurements. The electrical characteristics of each electrode are determined by elements of construction such as electrode size, the type of gel used, and the types of metals and other materials used in constructing the electrode. These electrical characteristics may be measured in the same manner as the offset potential by arranging an electrode pair in face to face relationship. The electrode pairs used for the device 10 must exhibit parameters within the following ranges:

| | |
|---|---|
| 1. DC Offset | 0–1.0 millivolts |
| 2. Offset Drift | 0–10 millivolts/second |
| 3. DC Resistance | 0–50 ohms |
| 4. AC Impedance | 0–50 ohms at 10 HZ |
| (impedance-frequency curve) | 0–15 ohms at 100 HZ |
| | 0–30 ohms at 1000 HZ |
| | 0–25 ohms at 10,000 HZ |
| | 0–25 ohms at 100,000 HZ |

Obviously, a single electrode cannot exceed the above parameters, and ideally, each single electrode will have parameters within a range which is one half the range indicated above for an electrode pair.

Rather than employing the address chip 88 to identify an electrode array, electrical characteristics unique to a specific type of acceptable electrode array can be sensed by the control unit 44 during an initialization period, and if one of these characteristics does not match stored characteristic parameters, no measurement operation is initiated. One of these electrode characteristics, an acceptable DC offset level has previously been discussed, but the DC resistance, and capacitance of the electrode array as well as the impedance of the array to various frequencies of AC current can be measured to identify an acceptable array.

Figure 3:
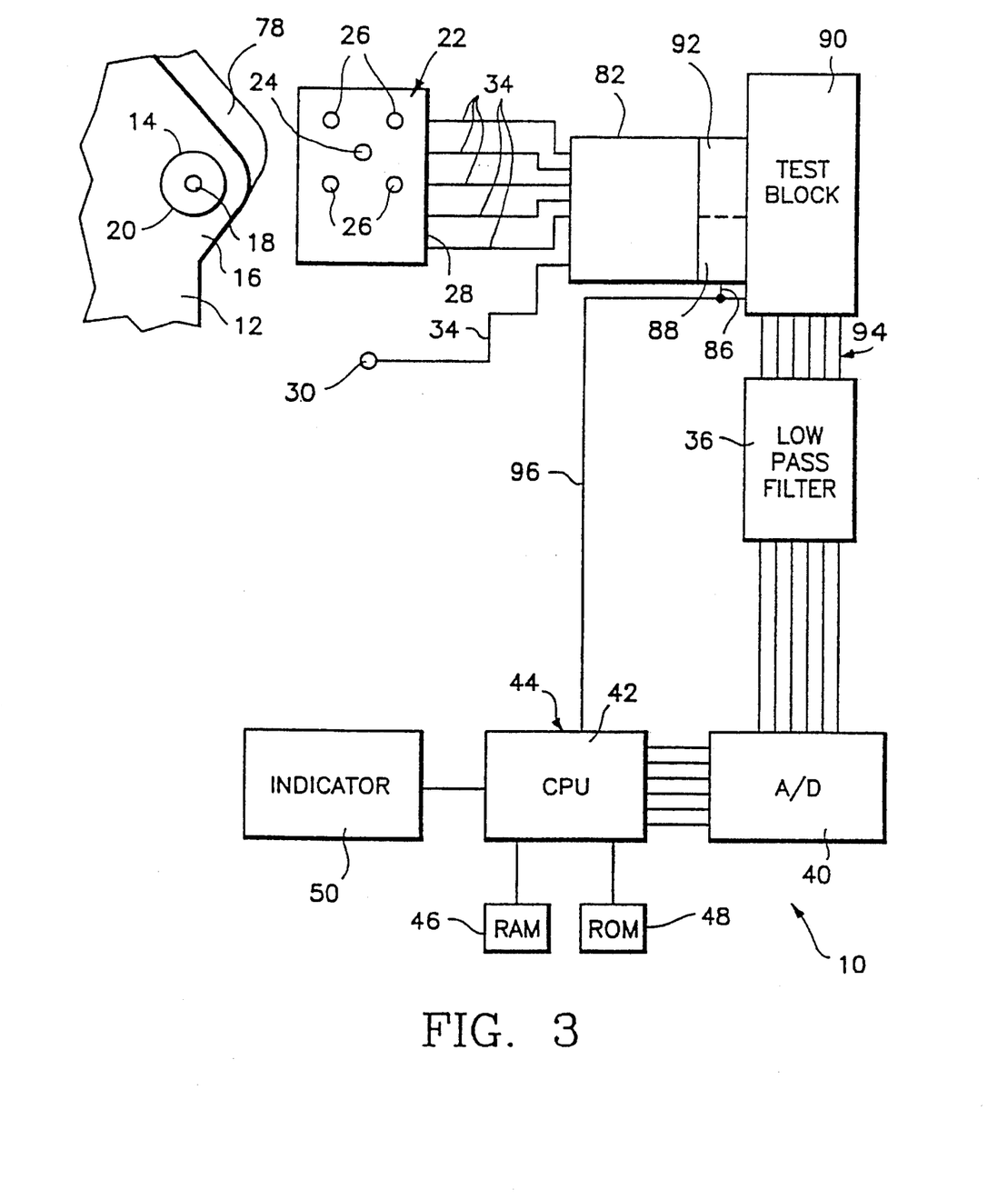
FIG. 3 is a block diagram of a second embodiment of the Apparatus For Screening And Diagnosing Trauma Or Disease In Body Tissues of the present invention.

Since AC frequencies will be filtered by the low pass filter 36, the cable 82 is connected to a test block 90 by a connector 92 as shown in FIG. 3. The lines 34 are connected by the connector 92 to corresponding lines within the test block which extend out from the test block at 94 to the low pass filter 36. A test connection 96 extends from the CPU 42 to the test block 90 to provide control signals on each of the leads 34 and to receive return signals therefrom. With the electrode array 22 connected, preferably with the shorting strip 80 in place as shown by the array 52, a DC signal can be applied by the CPU over the test connection 96 and the lines 34 to enable the CPU to sense the DC resistance of the array 22. If the sensed DC resistance does not match an acceptable resistance value stored in the memory of the control unit 44, the CPU will not initiate a biopotential measuring operation.

The capacitance of the electrode array could also be sensed in the same manner with a signal from the CPU over the test connection 96 to the test block 90 and the leads 34. The sensed capacitance indicated by return current flow to the CPU could then be compared with a stored capacitance value desired for an acceptable electrode to determine whether or not the CPU will initiate a biopotential measurement or will cancel the programmed measurement cycle until an electrode array with a capacitance matching the stored value is connected to the test block.

A very unique identifier for an electrode array is the impedance of the array to various frequencies of AC current. A specific electrode array impedance-frequency curve can be stored in the central controller 44, and during an initialization period, the CPU 42 will send an AC signal over the test connection 96 having a frequency which will generate the stored impedance-frequency curve in an acceptable electrode array. This AC signal is placed on the leads 34 in the test block and the return signal to the CPU over the test connection will be indicative of the impedance-frequency curve of the electrode array. When this curve matches the stored curve for arrays of the type tested, the CPU 42 will initiate a biopotential measurement operation at the end of the initialization period. Otherwise, in the case of a significant mismatch, no biopotential measurement operation will be begun.

The impedance, capacitance and impedance- frequency curve of two electrodes or a plurality of electrode pairs can be sensed in the manner described so long as the electrodes are in face to face relationship to form a battery. However, if they are stored and shipped in this condition without being short circuited, a DC offset potential is likely to be developed.

The use of electrode array electrical characteristics as an array identifier may provide the significant advantage of assuring that each array is manufactured to close tolerances. The optimum DC resistance, capacitance and AC impedance-frequency curve for an effective electrode or electrode array can be determined, and each array to be used for DC biopotential measurement should be manufactured to tolerances which provide such optimum electrical characteristics. When these characteristics are employed as an array identifier, the system is actually checking the quality control employed in the manufacture of the array.

For array identification purposes, it is important to recognize that one or more of the identifiers previously discussed may be combined during the initiation period, and if any of the identifiers is not sensed, the CPU 42 will not initiate a biopotential measuring cycle. For example, the connector 92 may include the address identification chip 88, and one of the signals sent over the test connection 96 by the CPU 42 would be the address identification signal. Subsequently or previously to this, the CPU could test for any or all of the electrical characteristics of the electrode array 22 and for the presence of an unacceptable offset potential.

It is important to recognize that the CPU 42 can be programmed to run identification tests on a variety of electrode combinations, since diverse DC biopotential measurement applications require the use of different numbers of electrodes. Thus, the electrical characteristics of as few as two electrodes, a reference and a measurement electrode, plus a plurality of acceptable electrode array combinations would be stored in the memory of the control unit 44. It is also possible to provide each individual electrode with an address identification chip 88 having a lead or terminal 86 which could plug into the test block 90. This would permit each individual electrode to be used during a measurement operation to be identified by the CPU 42 during an initialization operation.

Although the unit 88 has been identified as an address identification chip, this unit could constitute any structure which responds to an interrogation signal in a definable manner to identify either an electrode or an electrode array.

For example, the unit 88 could be formed by a particular material having a specific response characteristic to an interrogation signal, and this material could actually be one which is used in the construction of the individual electrodes.

Figure 4:
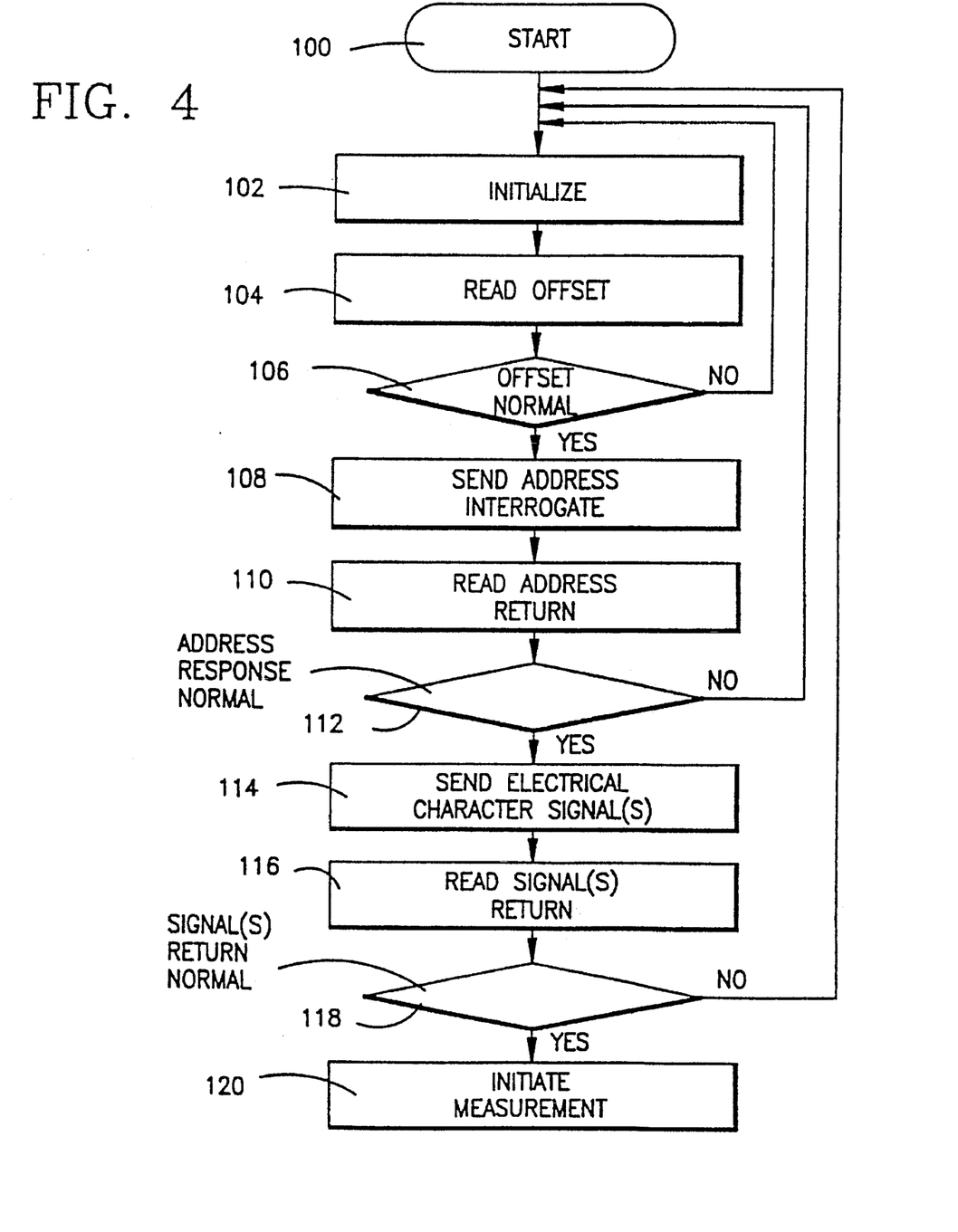
FIG. 4 is a flow diagram illustrating the operation of the Apparatus For Screening And Diagnosing Trauma Or Disease In Body Tissues during an initiation stage of operation.

The operation of the central controller 44 will be better understood with reference to the flow diagram of FIG. 4 which discloses the steps taken to check and identify the electrode array during the initialization period. In FIG. 4, all identification steps previously described are accomplished during the initialization period, but it must be recognized that any combination of these steps can be employed or that only one of these steps might be used.

The operation of the unit 10 is started by a suitable start switch as indicated at 100 to energize the central controller 44 and this triggers an initiate state 102. In the initiate state, the various components of the device 10 are automatically brought to an operating mode with, for example, the indicator 50 being activated while various control registers for the CPU 42 are reset to a desired state. At this point, the electrode checking operation is begun.

At 104 the offset potential present in the electrode array is sensed, and at 106 is compared to the acceptable normal offset level stored in the central controller 44. If the offset is not normal, the programmed operation is not continued until a normal reading is obtained.

As previously indicated, this may be the only electrode check made by the CPU 42, but regardless of other electrode array identification checks which may be made, it is beneficial to make an offset potential check to make certain that an electrode array with an acceptable offset voltage condition is present.

The CPU 42 operates at 108 to send an address interrogate signal or signals to the electrode array or individual electrodes, and at 110 reads the return signal or signals from the address chip or chips 88. If a normal address return is received which corresponds to the address stored in the central control unit 44, the programmed operation is continued, but upon receipt of an unacceptable address signal, the programmed operation is not initiated until an acceptable address return is received.

At 114, the CPU 42 sends one or more of the various array electrical characteristic interrogation signals to the electrode array, and at 116, the return from each of these signals is read. Again if any return does not correspond to the stored reference returns for an array of the type tested, the programmed operation is not continued, but if the return and reference signals correspond, the biopotential measurement program is initiated at 120.

As previously indicated, one or any combination of the electrode identification steps shown in the flow diagram of FIG. 4 may be used to initiate measurement at 120. Thus measurement initiation may be controlled directly from the offset comparison at 106 and steps 108–118 would be eliminated. If steps 104, 106 and 114–118 were eliminated, measurement initiation would be controlled directly by the address comparison at 112, and if steps 104–112 were eliminated, measurement initiation would be controlled by the comparison at 118 resulting from one or a combination of impedance, capacitance or impedance-frequency curve checks. The most preferable method for controlling measurement initiation, however, is to combine the offset check with at least one and possibly more of the other checks. Thus measurement initiation would be controlled by a combination of the comparisons at 106 and 112 or 106 and one or more of the comparisons at 118.

Although an actual measurement cycle may begin immediately after the identification steps of FIG. 4 have been completed, it is preferable to have the central processing unit 42 initiate a monitoring period once the electrodes have been placed on a patient and before an actual measuring cycle is begun.

When initially testing a patient for either a disease or traumatic condition by taking a DC biopotential measurement, it is necessary that the conditions in the test area be stabilized before reliable measurements of DC signals can be obtained. Many variables affect the ability to accurately measure biopotentials in a test area. For example, skin conditions vary, the gel used with sensing electrodes takes time to establish good contact, and numerous other factors affect the "settle down" time that is required before a stabilized signal can be sensed. The time required for the patient to "settle down" varies between species and also for individuals within the same species, so consequently, some time period must lapse before reliable measurements of DC signals can be taken. Previously, a preset waiting period of ten minutes or more was allotted to assure that the patient was "settled down", but much of this time was often wasted in that for some patients the "settle down" time is significantly less than the ten minute waiting period. An operation for determining when an adequate "settle down" time has passed for a particular patient is carried out by the central processing unit 42 in accordance with the flow diagram of FIG. 5. As can be seen from FIG. 5, once the unit 10 has been started at 100 and the central processing unit has been programmed through the initialize state 102, the presence of stable DC signals must be sensed before an accurate screening or diagnosing operation is begun. Because DC activity from the skin surface is monitored in a continuous manner, once the DC signals obtained in an initial predetermined monitoring period 122 are within a predetermined tolerance of the average potential in millivolts calculated from all measurements over that monitoring period, actual recording of the potentials can be initiated at 124. If all such measurements within the monitoring period are not within the predetermined tolerance of an average reading, a new monitoring period will be set at 126 and the process repeated. A two-minute monitoring period has been determined to provide an indication of whether "settle down" has occurred, and subsequent periods can be of the same or shorter intervals. Such time periods set forth herein are for the purpose of illustration, and any time period may be chosen so long as a sufficient number of measurements are taken to assure that a sufficient settle-down time period has passed. Further, a preferred predetermined tolerance has been determined to be a peak to trough signal measurement of 10 mV difference from that of the average reading. Again, any predetermined tolerance from ±1 mV to ±100 mV may be adopted so long as accurate representative DC signals can be obtained following the monitoring period or periods. With this start-up operation, the recording of potentials would not begin until the monitoring test indicates that stable accurate and reliable measurements of DC signals can be taken. By performing such a start-up operation, individual differences in settle-down time are easily taken into account so as to assure accurate and reliable DC measurements from any given individual.

Figure 5:
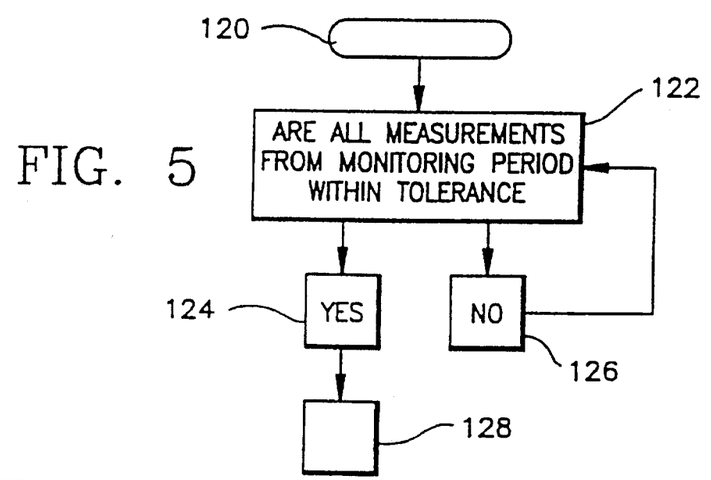
FIG. 5 is a flow diagram illustrating operation of the Apparatus for Screening and Diagnosing Trauma or Disease in Body Tissues during a premeasurement monitoring period.

The initial monitoring period 122 can be directly initiated after the initialize state 102 if no electrode characteristics are to be sensed, but when electrode characteristics are monitored, then the monitoring period will be triggered by a normal offset reading at 106, a normal address at 112, or a normal return signal at 118. Then, once the measurements taken during the monitoring period are within tolerance, biopotential measurements used for screening or diagnosis are begun at 128.

The importance of using electrodes having substantially no offset potential to obtain an accurate biopotential measurement has previously been stressed, and the depolarized pre-gelled electrode pair structure of FIG. 2 may be effectively employed for this purpose. However, many pre-gelled electrodes are packaged in face to face relationship or in other configurations without the conductive shorting strip 80, and these electrodes should not be used with the device 10 unless there is some assurance that they are depolarized. It may additionally be beneficial to predetermine whether or not the electrodes are formed with the electrical characteristics necessary to facilitate an accurate biopotential measurement, particularly if the device 10 is not programmed to perform the electrical characteristic tests of FIG. 4.

Figure 6:
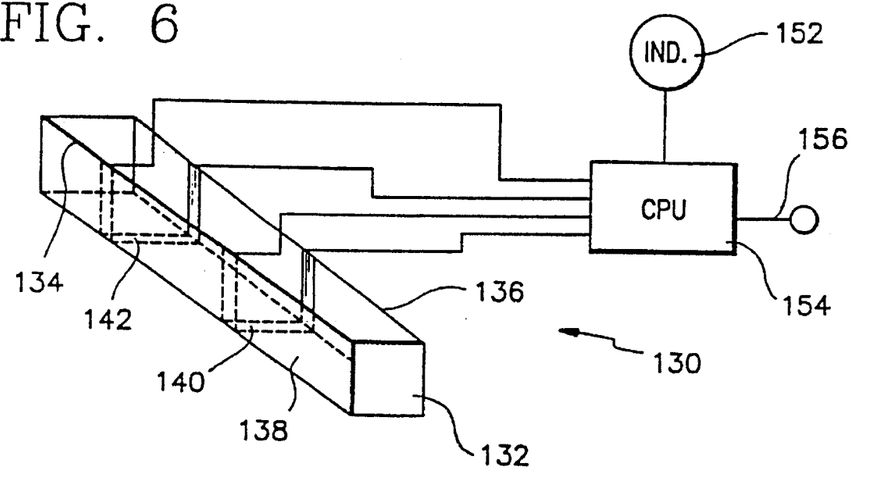
FIG. 6 is a block diagram of an electrode depolarizing and test unit.
Figure 7:
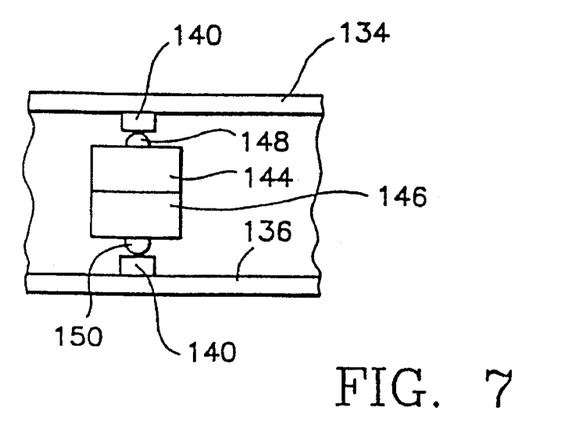
FIG. 7 is a partial plan view of the unit of FIG. 6.

Referring now to FIGS. 6 and 7, an electrode depolarizing and test unit indicated generally at 130 is illustrated which includes an electrode pair test section 132. The test section 132 includes sidewalls 134 and 136 which are joined by bottom wall 138. The walls 134, 136 and 138 may be of electrical insulating material or may include sections of electrical insulating material on which are mounted substantially U-shaped conductors 140 and 142. The U-shaped conductors form a short circuit conductive path similar to that formed by the conductive shorting strip 80 of FIG. 2.

To use the electrode depolarizing and test unit 130, two epidermal electrodes 144 and 146 of the type used for DC biopotential measurement are placed in face to face relationship so that the conductive gel present in each electrode contacts that of the opposite electrode. The electrode terminals 148 and 150 are placed in electrical contact with opposed legs of one of the U-shaped conductors which are supported by walls 134 and 136 of the electrode pair test section as shown in FIG. 7. Now the U-shaped conductor provides a short circuit path between the electrode terminals 148 and 150 to depolarize the electrode pair and reduce any offset potential which may be present.

Ideally, the electrode depolarizing and test unit 130 should include an indicator 152 which is electrically connected to the U-shaped shorting conductors to measure the offset potential in any electrode pair being depolarized and thus to indicate when this offset potential has been reduced to an acceptable level. The indicator 152 can be directly connected to the legs of the U-shaped conductors 140 and 142 at the portions thereof contacted by the terminals 148 and 150, but in FIG. 6, the indicator is connected to a microprocessor 154 which is in turn electrically connected to the U-shaped conductors 140 and 142. The microprocessor can sequentially connect one of a plurality of U-shaped conductors to the indicator 152, and any desired number of U-shaped conductors can be provided in the electrode pair test section 132.

When the microprocessor 154 is included in the electrode depolarizing and test unit 130, all of the electrical characteristic tests performed previously by the processing unit 42 as illustrated by the flow diagram of FIG. 4 can be provided by the microprocessor 154 which is connected to a suitable power source 156. Thus, the microprocessor 154 can not only provide an offset potential indication on the indicator 152, but can also test an electrode pair for capacitance, impedance, and for the frequency impedance curve of the pair. Indications for each of these electrical characteristics can be provided on the indicator 152, so there is no need to perform the test of FIG. 4 with the central processor 42 of FIG. 1. Instead, these tests are made separately in the electrode depolarizing and test unit 130 of FIGS. 6 and 7.

Figure 8:
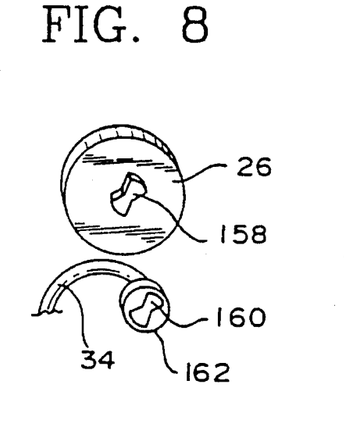
FIG. 8 is a perspective view of an electrode terminal connection for the electrodes of FIG. 1.

The electrodes 24, 26 and 30 of FIG. 1 may be mechanically configured to reduce the possibility that an electrode having the wrong electrical characteristics will be connected to the device 10. As illustrated in FIG. 8, each of the individual electrodes can be provided with an uniquely shaped electrode terminal 158 which fits into a cooperative uniquely shaped socket 160 in a connector 162 secured to one end of a lead 34. Thus, the lead 34 cannot be connected to any electrode which is not provided with the uniquely shaped terminal 158, and only electrodes having electrical characteristics which render them suitable for use with the device 10 are provided with a terminal shape corresponding to the socket 160. Obviously, any uniquely shaped terminal and socket can be employed, and rather than having the terminal 158 formed as a male member and the socket 160 formed as a female member, the two may be reversed with the socket forming the terminal for the electrode 26 and with the projecting male member being formed on the connector 162.

When the electrodes 24, 26 and 30 are preconnected as an array to the leads 34 as illustrated in FIG. 3, then the terminal 92 may be provided with uniquely shaped and arranged prongs 164 which cooperate with correspondingly arranged and uniquely shaped sockets 166 in a connector 168. Again, as in the case of the individual electrode of FIG. 8, the uniquely shaped prongs 164 could be provided on the connector 168 while the receiving sockets 166 would then be provided upon the connector 92.

Figure 9:
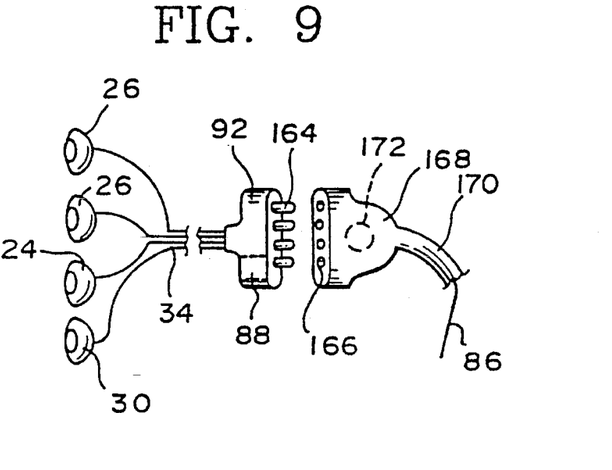
FIG. 9 is a perspective view of an electrode array connection for the electrode array of FIG. 1.

When using the connector 92 with the connector 168 of FIG. 9, the test block 90 of FIG. 3 may be eliminated and the multiple leads 170 from the connector 168 can be connected to the low-pass filter 36. However, one lead 86 from the connector 168 will be connected directly to the processor 42 to facilitate the electrical characteristic measurements previously described.

For some applications, it is possible to mount a battery 172 in the connector 168 and electrically connect this battery to one of the sockets 166 so that this batter will provide a signal to one of the prongs 164 of the connector 92 which is connected to the address chip 88. Thus, when the connectors 92 and 168 mate, the battery 172 will provide an address signal to the address chip 88, and if the proper address chip is present, an activate or start signal will be provided back over the lead 86 to the processor 42. This start signal might then directly initiate a measuring cycle by the device 10, may initiate the test cycle of FIG. 4, or may directly initiate the monitoring period of FIG. 5.

In FIGS. 1 and 3, the measuring electrode array 22 and the reference electrode or electrodes 30 have been shown as separate components, and each electrode is a conventional pre-gelled electrode formed of suitable conductive metals, such as silver/silver chloride, combined with a conductive gel of the type commonly used for biopotential electrodes. The reference electrode or electrodes 30 are often placed on the palm of a patient's hand or at some other location remote from the measuring electrode array 22 which, for example, may be applied to the patient's breast if breast cancer is being detected. However, the computations made by the device 10 rely, for accuracy, on stable biopotentials and a presumably constant reference signal from the reference electrode.

In actuality, the biopotential sensed by epidermal electrodes is a composite having variable sources, and thus potential is not necessarily constant over the duration of typical measurements. Once an epidermal electrode with a conventional conductive gel is fixed to the skin of a patent, a time-dependent junction potential is formed, and the same is true for the remote reference electrode 30. Other DC sources which effect the potential measurement are temperature and chemical effects. In fact, the change in the chemical composition of the skin is believed to be the second largest contributor to the measured biopotential signal after the offset and junction potentials.

Figure 10:
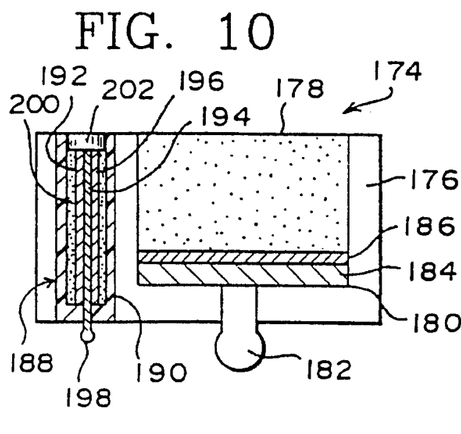
FIG. 10 is a sectional view of a biopotential electrode with an internal reference electrode for use with the apparatus of FIG. 1.

The reference electrode 30 is also subject to the formation of time dependent junction potentials, and if this electrode is significantly spaced from the measuring electrodes 24 and 26, there is a possibility that an entirely different junction potential as well as other interfering potentials may be formed in the reference electrode. One structure for eliminating a variable junction potential between the reference and measuring electrodes and creating a body-independent reference point is illustrated in FIG. 10, wherein an electrode indicated generally at 174 is formed to provide both a measuring electrode and an internal reference electrode. The measuring portion of the electrode 174 is constructed in substantially the same manner disclosed with respect to the pregelled electrodes 56a, 56b, 58a, and 58b of FIG. 2, and includes an insulating cup support member 176 which receives a conductive electrolyte gel 178. An electrode element 180 having a projecting terminal 182 completes the measuring portion of the electrode 174, and this electrode element may be formed from any conventional electrode materials, such as, for example, a silver layer 184 in contact with a silver chloride layer 186.

The cup 176 both spaces and insulates the measuring electrode portion of the electrode 174 from an internal reference electrode portion indicated generally at 188. The internal reference electrode includes a thin insulating casing 190 of teflon or similar material upon which is centrally mounted an elongated wire electrode 192. This wire electrode is formed of conventional electrode material, and for purposes of illustration, may be formed with a silver layer 194 surrounded by a silver chloride layer 196. A terminal 198 which projects outwardly from the cup 176 is connected to the wire electrode 192, and the casing 190 is filled with a solution of saturated potassium chloride or some other suitable conductive gel material 200. The end of the casing 190 opposite the terminal 198 is then closed with a frit or porous polyethylene plug 202.

When the electrode 174 is placed on the skin of a patient, both the measuring electrode portion and the internal reference electrode portion thereof will be subjected to substantially the same external conditions such as skin chemistry, temperature and other electronic and chemical effects. Thus, a DC biopotential measurement taken between the terminals 182 and 198 will not be subject to varying conditions which effect the measurement taken when the reference electrode is a substantial distance away from the measuring electrode, for a body-independent reference point has been created. In taking an actual measurement, two electrodes 174 may be used with the terminals 198 of the reference electrodes connected together, and this step will eliminate any drift caused by the gel creating a variable junction potential.

Due to the different metabolic requirements of cancerous cells, there is a strong likelihood that for select regions of the skin in the vicinity of such cells, a minute change in chemical composition may arise. When such is the case, it is possible that the non-selective electrodes previously described may not be the most effective way to exploit the localized chemical signals which occur. Instead, a more selective electrode which operates at the point of skin contact to pass ions associated with cancerous growth while excluding other ions will enhance the ability to detect malignant cells and facilitate a much earlier detection of malignant growths.

Figure 11:
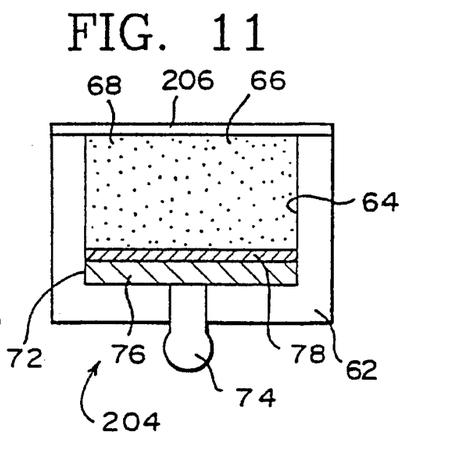
FIG. 11 is a sectional view of an ion selective biopotential electrode for use with the apparatus of FIG. 1.

In FIG. 11, a selective electrode indicated generally at 204 is formed using the electrode structure of one of the individual electrodes 56a, 56b, 58a, or 58b of FIG. 2, and reference numerals used for these electrodes are employed in FIG. 11 to indicate like-structural elements. In the electrode 204, the open end 66 of the electrode is covered by an ion exchange membrane 206 formed from ion exchange resin or similar material. The membrane 206 may be selected to pass only one kind of ion which is related to a specific malignant growth, or may be a polymeric ion-exchange membrane that permits only certain classes of ions to pass (like a cation-exchange membrane). A cation-exchange membrane would be a solid polymer membrane which allows only positively charged ions to migrate through to the conductive gel 68 while excluding the transfer of negatively charged ions to the gel. By providing an electrode with an ion exchange membrane which passes only ions or classes of ions associated with a specific type of cancerous growth, an electrode is provided having a much greater sensitivity to a minute change in the chemical composition which may arise at a select region of the skin due to the presence of cancerous cells. Of course, the electrode 174 of FIG. 10 may also be rendered selective by providing an ion exchange membrane 206 across the open end thereof to cover both the measuring electrode portion as well as the internal reference electrode portion.

What is claimed is:

1. A D.C. epidermal biopotential sensing electrode assembly for use with an apparatus for determining a cancerous condition at a test site on a human or animal subject as a function of an electromagnetic field present in the subject at that test site comprising:

a base, an electrode element mounted upon said base, an electrical terminal connected to said electrode element to conduct an electrical potential therefrom, and contact means mounted in contact with the electrode element for contacting the skin of the subject at the test site to facilitate the migration of ions associated with cancerous growth between the subject and the electrode element, said contact means including a conductive gel and a selective ion exchange means in contact with said conductive gel and operative to permit only ions having a particular electrical change to migrate between said subject and said electrode element while excluding other ions, said selective ion exchange means including an ion exchange membrane formed of an ion exchange resin mounted in contact with said conductive gel in spaced relationship to the electrode element.

2. The D.C. epidermal biopotential sensing electrode of claim 1 wherein said ions permitted to migrate between said subject and the electrode are only positively charged ions, said ion exchange resin being a solid polymer cation exchange material.

3. An apparatus for indicating a cancerous condition at a test site on a human or animal subject by measuring D.C. electrical biopotentials which are a function of an electromagnetic field present in the subject at said test site comprising:

a selective electrode sensing means which operates at a point of skin contact at the test site where a change in chemical composition may arise due to the presence of cancerous cells to detect D.C. biopotentials indicative of said electromagnetic field and provide output test potentials, said selective electrode sensing means including at least one epidermal D.C. biopotential sensing electrode to provide a reference electrode for contacting the skin of the subject at a reference site and at least one epidermal D.C. biopotential sensing electrode to provide a test electrode for contacting the skin of the subject at said test site, said test electrode including a base, an electrode element mounted upon said base, an electrical terminal connected to said electrode element to conduct an electrical potential therefrom, and contact means mounted in contact with the electrode element for contacting the skin of the subject at the test site to facilitate the selective migration of ions between the subject and the electrode element, said contact means including a conductive gel and a selective ion exchange means in contact with said conductive gel and operative to permit only predetermined ions to migrate between the subject and said electrode element, said selective ion exchange means including an ion exchange membrane mounted in contact with said conductive gel in spaced relationship to the electrode element, and processing means connected to receive said test potentials from said selective electrode sensing means, said processing means operating during a test period to sample a plurality of test potentials from said selective electrode sensing means.

4. The apparatus of claim 3 wherein said reference electrode and sensing electrode form a D.C. biopotential sensing electrode pair having a D.C. offset potential within a limited range of from 0 to 1.0 millivolts D.C.

5. The apparatus of claim 4 wherein said selective ion exchange membrane is formed of ion exchange resin, said ion exchange means operating to permit only ions having a particular electrical change to migrate between said subject and said electrode element.

6. The apparatus of claim 3 wherein said ion exchange membrane is a solid polymer cation-exchange membrane which permits only positively charged ions to migrate between said subject and the electrode element.

* * * * *